(12) United States Patent
Wortelboer

(10) Patent No.: US 10,004,631 B2
(45) Date of Patent: Jun. 26, 2018

(54) TONGUE MANIPULATION DEVICE, BONE ANCHOR FOR USE IN SUCH DEVICES AND AN ADJUSTMENT METHOD

(71) Applicant: KONINKLIJKE PHILIPS N.V., Eindhoven (NL)

(72) Inventor: Pippinus Maarten Robertus Wortelboer, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 957 days.

(21) Appl. No.: 14/373,941

(22) PCT Filed: Feb. 7, 2013

(86) PCT No.: PCT/IB2013/050997
§ 371 (c)(1),
(2) Date: Jul. 23, 2014

(87) PCT Pub. No.: WO2013/118069
PCT Pub. Date: Aug. 15, 2013

(65) Prior Publication Data
US 2015/0034094 A1    Feb. 5, 2015

Related U.S. Application Data

(60) Provisional application No. 61/596,784, filed on Feb. 9, 2012.

(51) Int. Cl.
*A61F 5/56*  (2006.01)
*A61B 17/04* (2006.01)
(Continued)

(52) U.S. Cl.
CPC ............... *A61F 5/56* (2013.01); *A61B 17/00* (2013.01); *A61B 17/0401* (2013.01);
(Continued)

(58) Field of Classification Search
CPC .. A61F 5/56; A61C 5/14; A61B 17/00; A61B 17/0401; A61B 17/24; A61B 2017/00407;
(Continued)

(56) References Cited

U.S. PATENT DOCUMENTS 7,975,700 B2 *  7/2011  Frazier ............... A61B 17/0401
                                              128/848
7,992,567 B2    8/2011  Hirotsuka
(Continued)

FOREIGN PATENT DOCUMENTS

CN      102198010         9/2011
WO      2007146338 A2    12/2007
WO      2012/041205       4/2012

*Primary Examiner* — Ophelia A Hawthorne
*Assistant Examiner* — Camtu Nguyen

(57) ABSTRACT

A bone anchor for a tongue manipulation device which has a tissue anchor for attachment to the tongue, the bone anchor, for example for attachment to the mandible and a tether line which fixes the tissue anchor to the bone anchor. The bone anchor has a spool arrangement with a indexing part and a spool part. In a first configuration the spool part is operable to spool the tether line without operation of the indexing part, and in a second configuration the spool part is operable to spool the tether line with operation of the indexing part. This means the spooling to take up slack in the tether line does not cause wear to the indexing springs, and it also means the user can feel when the slack has been taken up.

11 Claims, 5 Drawing Sheets

(51) Int. Cl.
*A61B 17/24* (2006.01)
*A61B 17/00* (2006.01)

(52) U.S. Cl.
CPC .... *A61B 17/24* (2013.01); *A61B 2017/00407* (2013.01); *A61B 2017/0404* (2013.01); *A61B 2017/044* (2013.01); *A61B 2017/0414* (2013.01); *A61B 2017/0417* (2013.01); *A61B 2017/0437* (2013.01); *A61B 2017/0464* (2013.01); *A61B 2017/0496* (2013.01); *A61F 5/566* (2013.01)

(58) Field of Classification Search
CPC .... A61B 2017/0404; A61B 2017/0414; A61B 2017/0417; A61B 2017/0437; A61B 2017/044; A61B 2017/0464; A61B 2017/0496
USPC .......................... 242/388, 396, 396.3, 396.4
See application file for complete search history.

(56) References Cited

U.S. PATENT DOCUMENTS

| | | |
|---|---|---|
| 8,081,859 B2 | 12/2011 | Toji |
| 2007/0144539 A1* | 6/2007 | van der Burg ..... A61B 17/0401 128/897 |
| 2008/0023012 A1* | 1/2008 | Dineen .............. A61B 17/0401 128/848 |
| 2008/0027560 A1* | 1/2008 | Jackson ............ A61B 17/0401 623/23.64 |
| 2008/0035160 A1* | 2/2008 | Woodson ................ A61F 5/566 128/860 |
| 2008/0208265 A1* | 8/2008 | Frazier ............... A61B 17/0401 606/326 |
| 2010/0161041 A1 | 6/2010 | Maisano et al. |

* cited by examiner ered when the rotary drive member is inserted into the bone anchor.

TONGUE MANIPULATION DEVICE, BONE ANCHOR FOR USE IN SUCH DEVICES AND AN ADJUSTMENT METHOD

CROSS REFERENCE TO RELATED APPLICATIONS

This application is a national filing PCT application Ser. No. PCT/IB2013/050997, filed Feb. 7, 2013, published as WO 2013/118069 A2 on Aug. 15, 2013, which claims the benefit of U.S. provisional application Ser. No. 61/596,784 filed Feb. 9, 2012, which is incorporated herein by reference.

FIELD OF THE INVENTION

This invention relates to a tongue manipulation device, and particularly to the design of the bone anchor used in such devices. It also relates to a method of adjusting such devices.

BACKGROUND OF THE INVENTION

It is known to use a tongue manipulation device to treat upper airway obstruction and sleep disordered breathing. Respiratory disorders during sleep are recognized as a common problem with significant clinical consequences. Obstructive Sleep Apnoea (OSA) causes an intermittent cessation of airflow. When these obstructive episodes occur, an affected person will transiently arouse. Because these arousal episodes typically occur 10 to 60 times per night, sleep fragmentation occurs which produces excessive daytime sleepiness. Some patients with OSA experience over 100 transient arousal episodes per hour. OSA may also lead to cardiovascular and pulmonary disease.

Various approaches are known which aim to maintain the airway passage during sleep. Oral appliances aimed at changing the position of the soft palate, jaw or tongue are available, but patient discomfort has limited their use. Continuous Positive Airway Pressure (CPAP) devices are often used as first-line treatments for OSA. These devices use a sealed mask which produces airflow at a slightly elevated pressure and acts to maintain positive air pressure within the airway.

This invention relates to an approach by which a tongue manipulation device is surgically applied to a patient. Aspire Medical was the originator of the "Advance" implantable tongue suspension technology.

The technology is described in detail in US2008/0023012 for example, on which FIGS. 1 to 3 are based.

The complete device comprises three essential parts:
(i) a tissue anchor which is surgically placed inside the tongue;
(ii) a bone anchor which is typically attached to the mandible; and
(iii) a tether line which fixes the tissue anchor to the bone anchor.

The bone anchor comprises a spool, enabling the surgeon to spool the tether into the bone anchor. This process is called titration and advances the tongue in the direction of the mandible (or prevents the tongue moving back), preventing blocking of the airway. The spool arrangement comprises an indexing part and a spool part, so that an audible sound is made during titration so that the degree of tightening can be judged. The indexing part can also retain the spool in a fixed position after adjustment or a separate lock can be used. The spool has a fixed number of stable positions over one spool revolution. Clockwise turning (for example) provides spooling up the tether line, and counter clockwise turning provides unspooling. The optimal advancement can be found by spooling back and forth.

Clinical studies have shown that the "Advance" technology is able to significantly reduce the number of apnoeic events in moderate and severe apnoea patients.

One possible issue with the known designs is that with the spool position held by the indexing mechanism (i.e. in the absence of a separate mechanical locking device) unspooling of the tether can arise over time, if the indexing part fails. The indexing part can for example have an indexer spring that forces the spool to take one of the stable positions (for example there may be six such positions). If the indexing part fails through reduced spring stiffness, the holding torque is lost, leading to unspooling of the tether. Each titration step loads the springs which step by step can degrade the holding function.

Another disadvantage of the known system is that it is difficult to feel whether the tether is tight or not as each indexed rotation requires a minimum torque to overcome the indexer springs. Thus, the user does not have a feel for the tether line tightness.

SUMMARY OF THE INVENTION

According to the invention, there is provided a device and method as claimed in the independent claims.

In one aspect, the invention provides a bone anchor for a tongue manipulation device which comprises a tissue anchor for attachment to the tongue, the bone anchor and a tether line which fixes the tissue anchor to the bone anchor,
wherein the bone anchor comprises a tether line spool arrangement, wherein the spool arrangement comprises an indexing part and a spool part, wherein in a first configuration the spool part is operable to spool the tether line without operation of the indexing part, and in a second configuration the spool part is operable to spool the tether line with operation of the indexing part.

The invention also provides the tongue manipulation system using the bone anchor.

This device enables indexed (i.e. ratcheted) titration to be carried out only after slack in the tether line has been wound onto the spool. Furthermore, when removing slack (without indexed rotation) the lack of resistance can be felt by the clinician before the tether line is tight. The bone anchor can for example be for attachment to the mandible.

In one arrangement, the spool part has an opening for receiving a rotary drive member, and the indexing part has an aligned opening for receiving the rotary drive member, wherein in the first configuration the rotary drive member engages only with the spool part and in the second configuration the rotary drive member engages with the spool part and the indexing part.

For example, the extent to which the rotary drive member is inserted into the device can dictate whether free spooling is possible or if indexed spooling is implemented. In this way, the rotary drive member functions to selectively couple the indexing part and the spool part together.

Alternatively, in the first configuration the indexing part is decoupled from the spool part, and in the second configuration the indexing part and the spool part are coupled together. Thus, the indexing part is not introduced until after the free spooling has been completed.

The indexing part can comprise spring loaded contact elements for contacting an outer face of the rotary drive member. In this way, the indexing function is only enabled when the drive member is inserted into the indexing part, since the rotary drive member itself defines the indexing surface.

In another aspect, the invention provides a method of adjusting a tongue manipulation device which comprises a tissue anchor for attachment to the tongue, a bone anchor and a tether line which fixes the tissue anchor to the bone anchor, wherein the method comprises:

spooling the tether line onto the bone anchor without any indexing operation until slack in the tether line is removed; and spooling the tether line onto the bone anchor with indexing to provide audible feedback of the degree of tether line titration.

BRIEF DESCRIPTION OF THE DRAWINGS

Examples of the invention will now be described in detail with reference to the accompanying drawings, in which.

DETAILED DESCRIPTION OF THE EMBODIMENTS

The invention relates to tongue manipulation devices having a tissue anchor for attachment to the tongue, a bone anchor typically for attachment to the mandible and a tether line which fixes the tissue anchor to the bone anchor. The bone anchor has a spool arrangement with an indexing part and a spool part. In a first configuration the spool part is operable to spool the tether line without operation of the indexing part, and in a second configuration the spool part is operable to spool the tether line with operation of the indexing part. This means the spooling to take up slack in the tether line does not cause wear to the indexing components, e.g. springs, and it also means the user can feel when the slack has been taken up.

The invention can be applied as a modification to known devices, for example of the type described in detail in US2008/0023012, which is hereby incorporated by reference.

The relevant parts of the known device will first be described, with reference to FIGS. 1 to 3 which are adapted from US2008/0023012.

Figure 1:
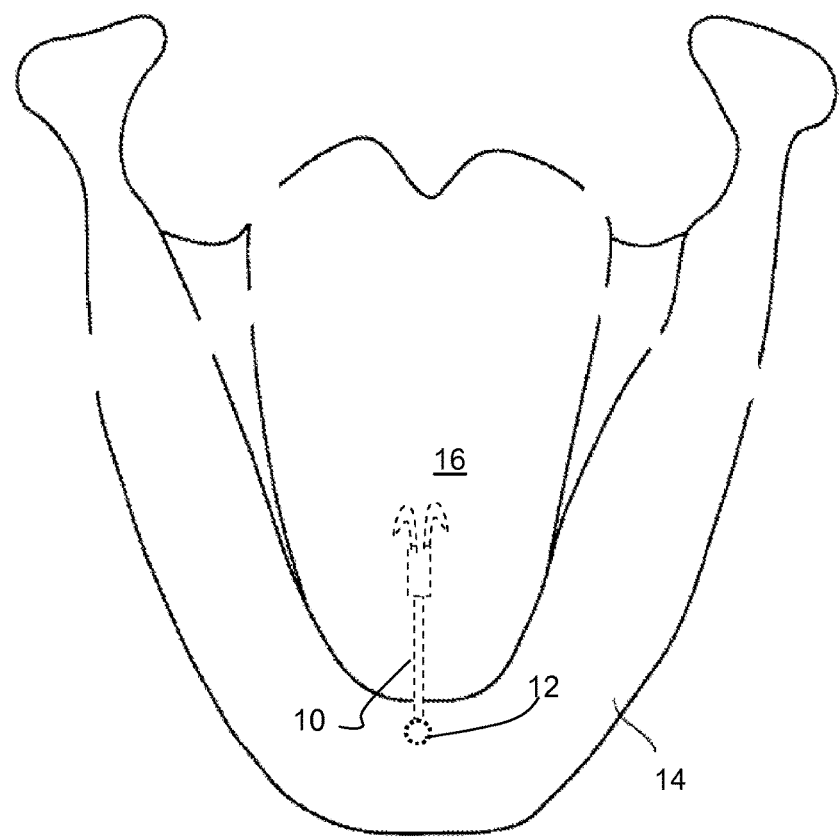
FIG. 1 shows generally how a known tongue manipulation device is used.

FIG. 1 shows a tongue manipulation device 10 attached to a securing assembly 12 located on the inferior surface of the mandible 14. The tongue is shown as 16.

Figure 2:
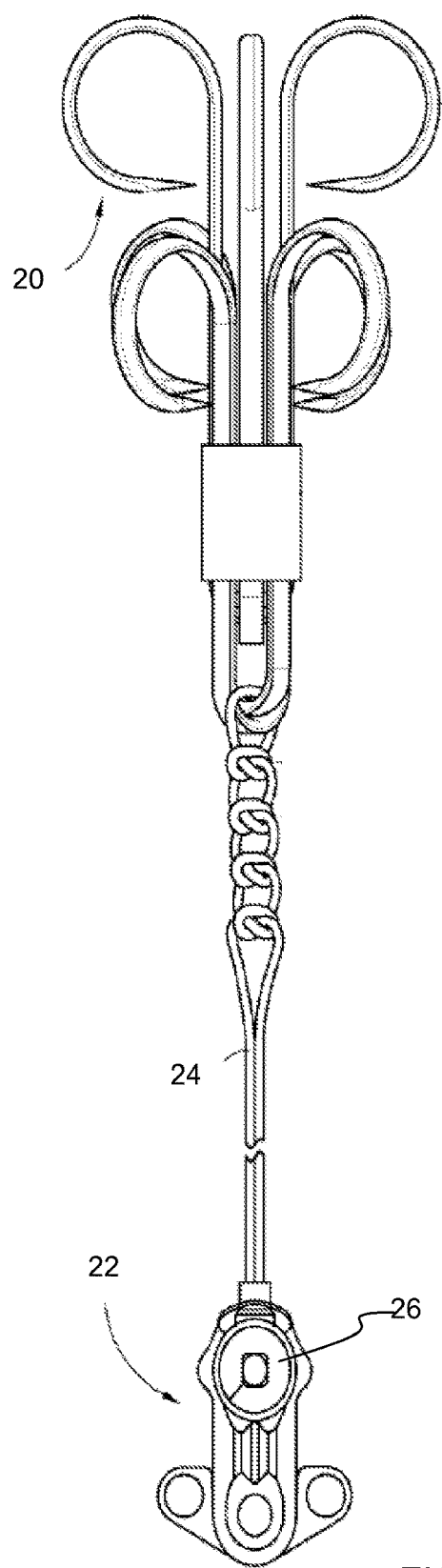
FIG. 2 shows the known tongue manipulation device in more detail.

FIG. 2 shows a possible design of the tongue manipulation device in more detail.

It comprises a tissue anchor 20 for attachment (in particular implantation) to the tongue and a bone anchor 22 for attachment to the mandible. A tether line 24 fixes the tissue anchor to the bone anchor.

The bone anchor 22 comprises a tether line spool arrangement 26. This enables the tether line to be wound onto the spool to take up slack in the tether line so that the line can provide a desired restricted movement of the tongue.

Figure 3:
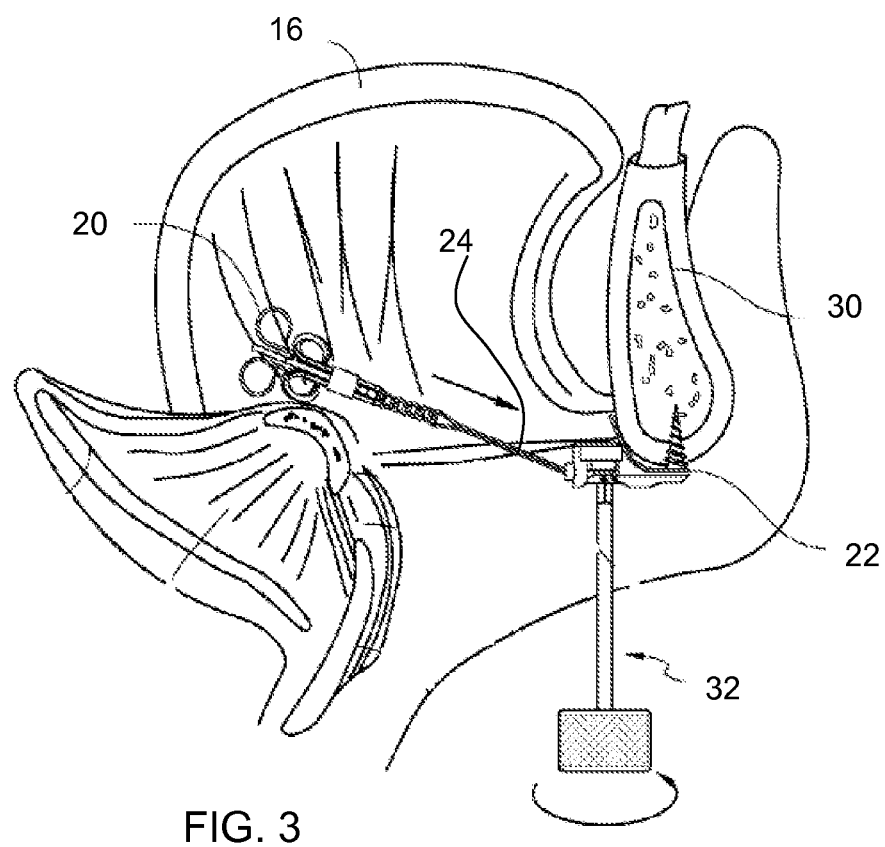
FIG. 3 shows how the tension in the tether line is adjusted in the device of FIGS. 1 and 2.

FIG. 3 shows how adjustment of the spool is made, and shows a cross section through the lower part of the head of a patient. The bone anchor 22 is attached to the lower mandible 30 as shown. To tighten the tether line 24, a rotary drive shaft 32 (known as a "titration needle") is inserted into an opening in the spool part of the bone anchor, and adjustment is judged based on an indexed function.

The invention provides an arrangement in which the indexing function can be selectively engaged or disengaged.

A first approach is to enable the titration needle (which is used to control the spooling) to be operable at two depth levels, one with the indexing function operable and one without. A second approach is to provide the indexing part as a component that can be added to the bone anchor after slack has been removed.

Figure 4:
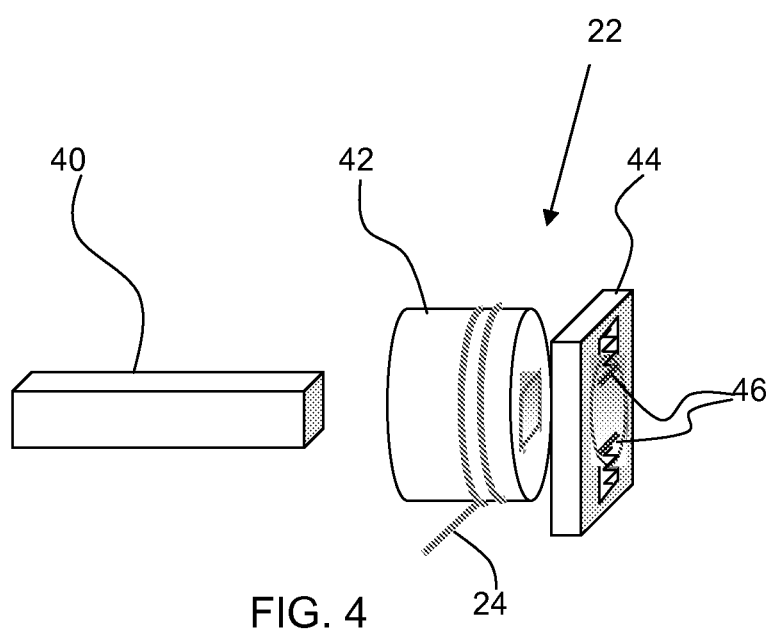
FIG. 4 shows in schematic form the concept of the tension adjusting arrangement of the invention for use in the device of FIGS. 1 to 3.

FIG. 4 shows in schematic form an example of the titration needle that can spool at two depth levels with and without indexer.

The titration needle 40 is shown with a square cross section. The bone anchor 22 has a spool part 42 and an indexing part 44. The spool part 42 can rotate freely using a standard needle 40 that is inserted in the spool center hole. Only when the titration needle 40 is pushed through a little resistance to the deepest level it engages in the indexing part 44 that is part of the bone anchor housing. Thus, instead of the spool having a cam arrangement to provide the indexing function, the titration needle itself defines the cams by virtue of its polygonal outer shape, and the outside of the spool can be perfectly round.

The principle functioning of the indexing part 44 is illustrated in schematic form by two indexing projections 46 on springs. These engage with outer faces of the titration needle 40 to provide indexed positions. Once engaged, the turning of the titration needle 40 is no longer free; it requires a torque to overcome the spring loads on the titration needle 40, and the rotation of the needle within the indexing part provides tactile as well as audible feedback of the adjustment made. Any type of spring element can be used, for instance cantilevered arms (click fingers) as shown in the more detailed examples below. Also other numbers of elements can be used in combination with needles that have the same number of facets or grooves.

When the indexing part 44 is not engaged, slack can be removed (for example clockwise) without the need to overcome the indexing forces (clicks). The spool rotation is unconstrained when the titration needle is only inserted in the spool hole and not in the indexing part.

Thus, in a first configuration the spool part is operable to spool the tether line without operation of the indexing part (the low depth insertion of the needle 40), and in a second configuration the spool part is operable to spool the tether line with operation of the indexing part (the full depth insertion of the needle 40).

When the user experiences an increase in resistance the slack is most probably gone and titration should start. At that point, the titration needle is pushed to a level deeper (after slight rotation angle adjustment if needed) and the needle tip engages in the indexing part which is part of the housing. In the titration stage it behaves as in the original device; titration steps can be felt and counted.

Once the titration achieves satisfactory advancement, the spool position needs to be fixed. The preferred locking method is to leave behind the needle head (similar to a screwdriver with interchangeable bits). Provided the spring force in the indexer part is strong enough, no further measures are needed. To minimize the risk of unspooling, the indexer spring can be designed to block the unspooling.

Figure 5:
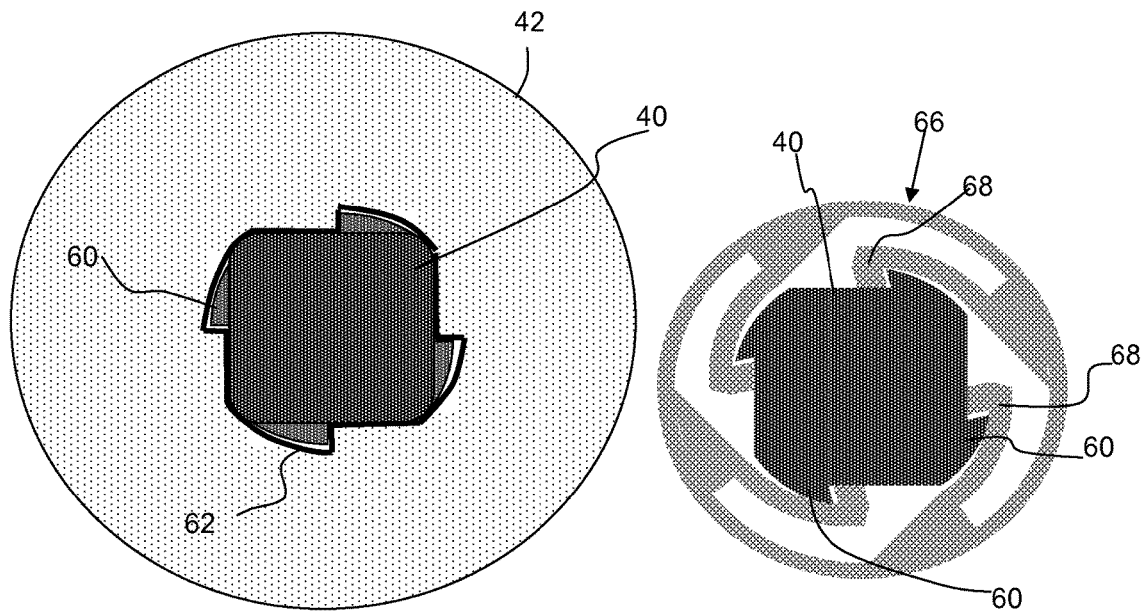
FIG. 5 shows a first example of tension adjusting arrangement of the invention for use in the device of FIGS. 1 to 3.

FIG. 5 shows a first example of arrangement of the invention in more detail. The spool part 42 and indexing part 66 are shown side by side, but the indexing part is in this example behind the spool part in the direction of insertion of the titration needle, as shown in FIG. 4.

The needle 40 has four corner extensions 60.

These corner fingers have a specific design at the end of the titration needle, where they engage with the indexing part 66, as shown in the right part of FIG. 5. Here, they define an undercut which gives secure engagement with the fingers 68. The corner extensions 60 may have a different shape where they pass through the spool opening, or they may not even be present at all on that part of the titration needle, since they are not needed for spooling—the square side faces alone are sufficient to ensure that the spool part and the indexing part cannot rotate relative to each other with the needle in place. The opening in the spool part only needs to allow the needle tip cross section to pass and to provide rotational locking to the needle.

The corner extensions 60 function as indexing features, in that they engage with the fingers 68 of the indexing part 66 to provide the audible clicking as well as causing the needle to be rotatable in one direction only. The spool 42 has a correspondingly shaped opening 62. The corner extensions 60 of the square needle 40 are provided at the distal end. The needle 40 can be inserted and passed through the hole in the spool 42. Free rotation is possible as long as the front of the needle is not pushed into the spring plate 66 which forms the indexing part. Once the needle is fully pressed into the spring plate 66, the counter-clockwise turning is blocked while the clockwise turning is still possible by a slight bending outward of the click fingers 68. The indexing part is fixed to the bone anchor housing so that it cannot rotate. It operates using the principle of a set of pawls (the spring loaded fingers 68) which engage with the teeth of a ratchet wheel. The pawls are spring biased by their shape radially inwardly to engage with the teeth.

Unspooling is not possible without breaking off the fingers 68. To unspool, the needle 40 is retracted such that free spool rotation is enabled again.

In principle a separate lock can be added, but this requires a second tool to push or screw in a blocking element. Only after this blocking element is in place and disables the spool to rotate, the titration needle can be withdrawn. Thus, it is simpler to use the end of the needle 40 as the locking element.

Leaving behind the needle part that has been inserted into the spool part and indexing part for fixing the spool position is possible by using any screwing tool consisting of two parts. The hand grip with the proximal part of the needle that is not pressed in the spool is disconnected at the end of the titration procedure. Any standard method can be used, but the most straightforward is a screw connection with a well chosen torque limit. The needle part in the spool can have an exterior screw thread and the hand grip has a screw nut of corresponding thread size and pitch. Connection is made by turning the grip clockwise. Thus, in titration (spooling up) the needle can never be disconnected. For desired back spooling, the needle is pulled out slightly such that the spool is free to rotate.

To finish the procedure, the tip is to be left locked in the indexer and the grip is turned counter clockwise. The tool will disconnect at a torque that the indexer click finger plate is able to withstand.

To create a small resistance to prevent the needle tip become dislodged over time, there are numerous features that can be added. If the clamping force of the click fingers and the friction coefficient of the contacting areas with the needle are sufficiently high there is no need for additional features. In case the friction can be critically low, straightforward modifications to the needle tip are possible. As an example, small bumps can be added at the end of the grooves in the needle in combination with click finger tips that have rounded edges. The bumps will deflect the fingers slightly in pressing the needle into the indexer first, but once the bumps have passed the finger tips, the tips fall back into the grooves right behind the bumps. This forms a gripping function in the direction of insertion of the titration needle, and which deflects the click fingers. To pull out, a similar small deflection of the click fingers is needed. This creates the resistance required for keeping the tip safely in the spool after the titration operation is finished.

As the hole in the spool remains occupied there is no room for biomaterial to grow in. This reduces the risk that some months after implantation the spool hole will be filled to an extent that the titration needle can no longer engage the spool for re-titration. In the proposed solution with the titration needle tip left in the implant, the grip part of the titration needle with the screw hole is to be used to locate the tip part in case re-titration is needed. Finding the screw end which projects out from the spool in a minimally invasive operation might be delicate, but once the screw end is captured the clockwise turning of the grip will establish a connection despite the biomaterial deposits provided the nut has sufficient capability to scrape off deposits similar as in self tapping/threading nut.

In the example of FIG. 5, the spring plate 66 is behind the spool part 42.

Figure 6:
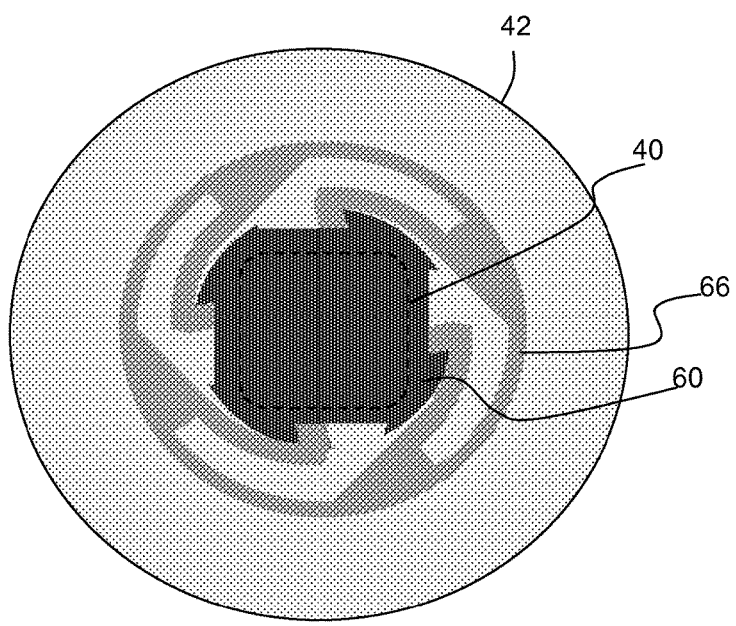
FIG. 6 shows a second example of tension adjusting arrangement of the invention for use in the device of FIGS. 1 to 3.

However, the spring indexing plate 66 can be in front of the spool part 42 as shown in FIG. 6.

The hole in the spool part 42 is square as is the needle tip. In this case, the collar of the needle has the four extensions that can engage in the spring plate 66 (indexer) when pressed fully in. The extensions are set back from the tip of the needle, by a distance based on the thickness of the spool part (and the length of the needle which extends past the indexing part when the needle is fully engaged). Again, only turning in one direction is then possible. To unspool, the needle is retracted a bit. To secure the final spool position the needle tip including collar is left inside the spool.

The fitting of the device of the invention is possible within the standard procedure for implanting a bone anchor. The bone anchor is screwed onto the mandible right after the tether (which is coupled to the tissue anchor) has been attached.

The slack in the tether can be removed using a torque limited needle. In this way, the rotary drive of the needle will cut off when a preset torque is reached, corresponding to the removal of slack.

In the examples above, the degree to which the titration needle is inserted determines whether or not the indexing part is engaged. However other solutions are possible. For example, the indexing part can be applied as a cap over the spool part after the slack has been taken up. Thus, once the slack has been removed, a cap can be mounted with the indexing part inside. After slack has been taken up, there is almost no tether tension, so the titration needle can be removed, the cap fitted and the titration needle re-introduced for the indexed adjustment.

Thus, in a first configuration the indexing part is decoupled from the spool part (the cap is not present), and in a second configuration the indexing part and the spool part are coupled together (the cap is present).

From then on, the device behaves as a standard spool in titration. The advantage is again that the clicking mechanism is not subjected to unnecessary slack removal clicks.

The mounting of the cap which incorporates/completes the indexing mechanism can be achieved in many ways: screwing or a snap fit are both feasible. There is still freedom of choice in where to implement the indexer spring elements. They can be in the housing as in the previous embodiment, but also in the cap itself.

The third example, of the use of a cap, results in a more cumbersome procedure. The first and second examples, of FIG. 5 or 6, are therefore preferred. However, the concept of the invention, to provide non-indexed spooling followed by indexed titration can be implemented in various ways including the three examples given above.

It will be clear that the invention resides in the spooling arrangement forming part of the fixed bone anchor part. The invention thus relates to the bone anchor part in isolation as well as to the tongue manipulation device as a whole.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A bone anchor for a tongue manipulation device which comprises a tissue anchor for attachment to the tongue, the bone anchor and a tether line which fixes the tissue anchor to the bone anchor, wherein the bone anchor comprises:
    a tether line spool arrangement comprising an indexing part and a spool part,
    wherein the spool part has an opening for receiving an associated rotary drive member, and the indexing part has an aligned opening for receiving the associated rotary drive member,
    wherein in a first configuration the associated rotary drive member engages only with the spool part and is operable to spool the tether line without operation of the indexing part, and in a second configuration the associated rotary drive member engages with both the indexing part and the spool part and is operable to spool the tether line with operation of the indexing part.

2. A bone anchor as claimed in claim 1, wherein the indexing part comprises spring loaded contact elements for contacting an outer face of the associated rotary drive member.

3. A bone anchor as claimed in claim 1, wherein the indexing part is behind the spool part with respect to the direction of insertion of the associated rotary drive member, and the associated rotary drive member has indexing features at a distal end of the associated rotary drive member.

4. A bone anchor as claimed in claim 1, wherein the indexing part is in front of the spool part with respect to the direction of insertion of the associated rotary drive member, and the associated rotary drive member has indexing features set back from a distal end of the associated rotary drive member.

5. A bone anchor as claimed in claim 1, wherein in the first configuration the indexing part is decoupled from the spool part, and in the second configuration the indexing part and the spool part are coupled together.

6. A tongue manipulation system, comprising:
    a tissue anchor for attachment to the tongue;
    a bone anchor including a spool arrangement comprising an indexing part and a spool part;
    a tether line which fixes the tissue anchor to the bone anchor; and
    a rotary drive member having a non-circular outer shape;
    wherein the spool part of the spool arrangement has an opening for receiving the rotary drive member, the spool part opening having a corresponding shape; and
    wherein (i) in a first configuration the rotary drive member is inserted at a first depth to engage the spool part of the spool arrangement but not the indexing part of the spool arrangement whereby rotation of the rotary drive member operates to spool the tether line without operation of the indexing part, and (ii) in a second configuration the rotary drive member is inserted at a second depth to engage both the spool part of the spool arrangement and the indexing part of the spool arrangement whereby rotation of the rotary drive member operates to spool the tether line with operation of the indexing part.

7. A system as claimed in claim 6, wherein the rotary drive member has a polygonal outer shape.

8. A system as claimed in claim 7, wherein the indexing part comprises a plurality of spring loaded contact elements for contacting outer faces of the rotary drive member.

9. A method of adjusting a tongue manipulation device which comprises a tissue anchor for attachment to the tongue; a bone anchor and a tether line which fixes the tissue anchor to the bone anchor, wherein the method comprises:
    spooling the tether line onto the bone anchor without any indexing operation until slack in the tether line is removed; and
    after the slack in the tether line is removed, spooling the tether line onto the bone anchor with indexing to provide audible feedback of the degree of tether line titration.

10. A method as claimed in claim 9, comprising inserting a rotary drive member into an opening of a spool part for spooling without indexing, and further advancing the rotary drive member also into an aligned opening of an indexing part for spooling with indexing.

11. A method as claimed in claim 9, comprising inserting a rotary drive member through an opening of an indexing part and into an opening of a spool part for spooling without indexing, and further advancing the rotary drive member so that engagement features of the rotary drive member which are set back from the tip of the rotary drive member come into engagement with the opening of the indexing part for spooling with indexing.

* * * * *